(12) United States Patent
Lin et al.

(10) Patent No.: US 8,916,207 B2
(45) Date of Patent: Dec. 23, 2014

(54) CORNEAL COVER OR CORNEAL IMPLANT AND CONTACT LENS AND METHOD THEREOF

(75) Inventors: Chien-Cheng Lin, Taipei (TW);
Horng-Ji Lai, Taipei (TW);
Shang-Ming Lin, Fongyuan (TW);
Feng-Huei Lin, Taipei (TW)

(73) Assignee: Body Organ Biomedical Corp., Taipei (TW)

( * ) Notice: Subject to any disclaimer, the term of this patent is extended or adjusted under 35 U.S.C. 154(b) by 768 days.

(21) Appl. No.: 12/659,282

(22) Filed: Mar. 3, 2010

(65) Prior Publication Data

US 2010/0241224 A1    Sep. 23, 2010

Related U.S. Application Data

(63) Continuation-in-part of application No. 11/882,328, filed on Jul. 31, 2007, now Pat. No. 7,838,038.

(60) Provisional application No. 60/868,409, filed on Dec. 4, 2006.

(51) Int. Cl.
| | |
|---|---|
| *A61K 35/60* | (2006.01) |
| *A61F 2/14* | (2006.01) |
| *A61L 27/36* | (2006.01) |
| *A61L 27/56* | (2006.01) |
| *B29D 11/00* | (2006.01) |
| *G02B 1/04* | (2006.01) |

(52) U.S. Cl.
CPC .......... *A61L 27/3641* (2013.01); *A61L 27/3604* (2013.01); *A61L 27/56* (2013.01); *B29D 11/00038* (2013.01); *G02B 1/043* (2013.01)
USPC ........................... 424/520; 424/522; 424/427

(58) Field of Classification Search
USPC .................................................. 424/520, 522
See application file for complete search history.

(56) References Cited

U.S. PATENT DOCUMENTS

| | | | |
|---|---|---|---|
| 2002/0006422 A1 | 1/2002 | Koda et al. | 424/401 |
| 2003/0118715 A1 | 6/2003 | Helgason | 426/624 |
| 2009/0036656 A1* | 2/2009 | Lai et al. | 530/427 |

OTHER PUBLICATIONS

Lin et al., A New Fish Scale-derived Scaffold for Corneal Regeneration, European Cells and Materials, Feb. 26, 2010, vol. 19, pp. 50-57.*
"Animal Diversity Web, Tilapia", Dec. 2012, http://animaldiversity.ummz.umich.edu/accounts/Tilapia/classification/.*
"Class Osteichthyes" Bony Fishes, chapter 6, Dec. 2012, http://users.tamuk.edu/kfjab02/Biology/Vertebrate%20Zoology/b3405_ch08.htm.*

* cited by examiner

*Primary Examiner* — Ruth Davis
(74) *Attorney, Agent, or Firm* — McClure, Qualey & Rodack, LLP

(57) ABSTRACT

A corneal cover or corneal implant to be placed within or onto the surface of the cornea is made of bony fish scales and a contact lens is made of bony fish scales.

7 Claims, 1 Drawing Sheet

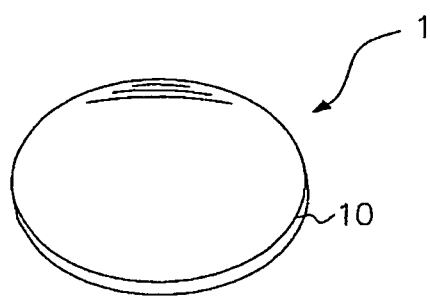
F I G .1
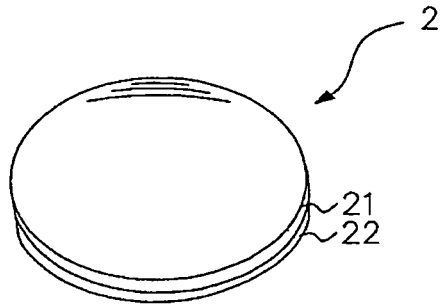
F I G 2
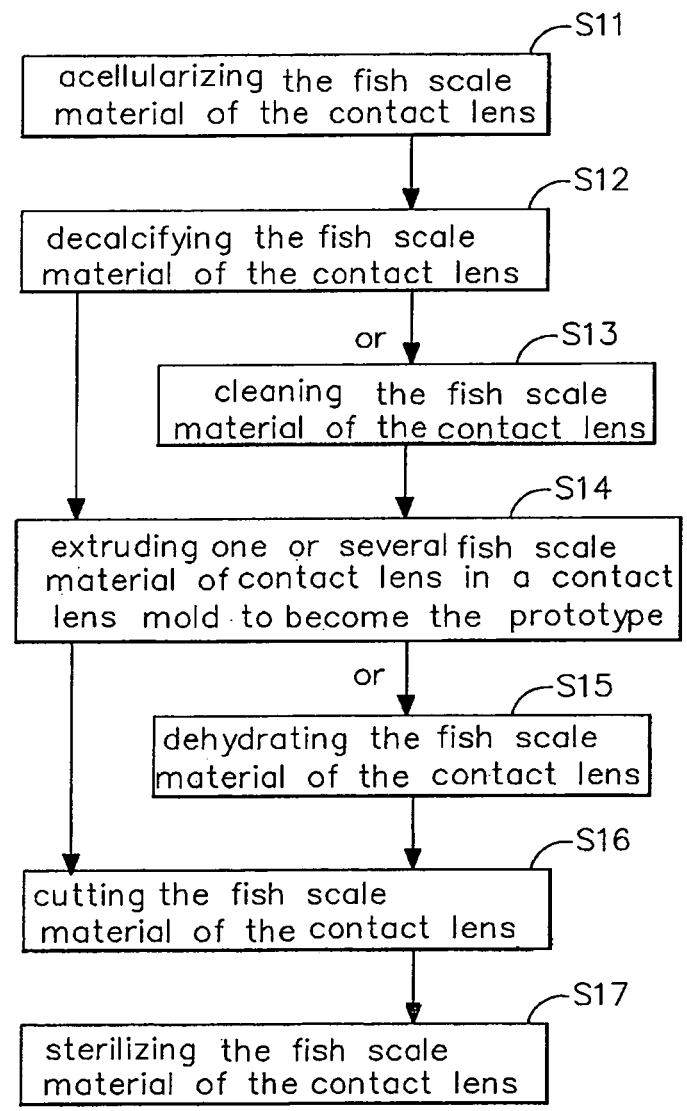
F I G .3

CORNEAL COVER OR CORNEAL IMPLANT AND CONTACT LENS AND METHOD THEREOF

This patent application is a Continuation In Part (CIP) to the application Ser. No. 11/882,328 Filed Aug. 18, 2009 Title: BIOMATERIAL AND PREPARATION METHOD THEREOF (Mother Application), which is still pending.

FIELD OF THE INVENTION

This invention relates to an artificial corneal cover or corneal implant, and an artificial contact lens and the method thereof.

BACKGROUND OF THE INVENTION

The human cornea is a multilayered structure, having five principal layers. Loss of sight caused by corneal damage or pathological changes is one of the most common ophthalmologic diseases.

In surgical treatment for ocular-surface diseases in which the cornea is covered with the conjunctival epithelium to cause haze, at the present time, corneal epithelium transplantation is carried out.

However, transplantation of a cornea not only has difficulties such as securing the source of donation, but immunological rejection often leads to failures in the transplantation. Accordingly, scientists have attempted to use animal corneas to treat corneal diseases in humans, including studies performed on the direct transplantation of animal corneas. However, such direct animal corneal transplantations were unsuccessful because of immunological rejection. Additional research on preparations of artificial corneas from animal corneas by low-temperature freezing and simple sterilization treatment were also unsuccessful because the elimination of antigens was not complete and the patients' bodies could not accept the transplants due to poor tissue compatibility.

Besides, another kind of artificial cornea material is made of monomers. However, the conventional process to make artificial cornea for producing silicon-containing materials typically fail to provide satisfactory yield and purity while retaining advantageous transparency and oxygen permeability.

Thus, there still remains a need for an effective artificial cornea that can be harvested from animal corneas.

On the other hand, man has attempted to correct and adapt his conditions to enjoy perfect vision, or to endow it with greater resources for centuries. Diverse instruments have been invented toward this end, including spectacles, magnifier, contact lens, etc. Contact lenses that exhibit high oxygen permeability are generally preferred for the health and comfort of the eye.

Generally, a contact lens material having oxygen permeability contains a silicone (meth)acrylate or silicone styrene as a main component, and other components, in order to impart contamination resistance, strength and the like, a monomer adjusted with each objective performance is selected as a copolymerizing component and polymerized.

However, since the structure and characteristic of a polymerization part of each monomer are different in the case of the copolymerization in a multi-component system, it was fundamentally difficult to favorably copolymerize them, and experience and know-how were entrusted in many cases. Therefore, very long time and labors are required in order to provide better copolymerization with excellent productivity and complete end products.

Therefore, it is desirable to provide another contact lens material that eliminates the aforesaid drawbacks.

BRIEF SUMMARY OF THE INVENTION

It is an aspect of the invention to provide a corneal cover or corneal implant to be placed within or onto the surface of the cornea, and the corneal cover or corneal implant is made of bony fish scales. In an embodiment of the invention, the shape of the corneal cover or corneal implant is curvature and the diameter of the corneal cover or corneal implant is about 5-11 mm. Further, the thickness of the corneal cover or corneal implant is 0.03-0.8 mm.

It is another aspect of the invention to provide a contact lens which is made of bony fish scales.

It is one method for preparing a contact lens from bony fish scales comprising the step of acellularizing the bony fish scales, decalcifying the bony fish scale material, extruding one or several bony fish scale material in a contact lens mold to become the prototype, cutting the bony fish scale material and sterilizing the contact lens.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 illustrates a schematic view of a first preferred embodiment of the present invention.

FIG. 2 illustrates a schematic view of a second preferred embodiment of the present invention.

FIG. 3 illustrates a flow chart of a second preferred embodiment of the present invention.

DETAILED DESCRIPTION OF THE INVENTION

Reference will now be made in detail to the present embodiments of the invention, examples of which are illustrated in the accompanying drawings.

Referring to FIG. 1A and FIG. 1B, the present invention relates to a corneal cover or corneal implant 1 prepared from bony fish scales 10. The corneal cover or corneal implant 1 is made of bony fish scales so as to be placed within or onto the surface of the cornea.

The corneal cover or corneal implant 1 in an eye of a patient is to increase the depth of focus of the patient includes an anterior surface. In accordance with some examples of the invention, the bony fish scale material 10 is chosen from bony fish which is selected from the group consisting of the cycloid scale, and the ctenoid scale.

The corneal cover or corneal implant 1 is biocompatible, optically transparent, and synthetic. In a specific example of the invention, the shape of the corneal cover or corneal implant 1 is curvature and the diameter of the corneal cover or corneal implant 1 is the same with the cornea taken from patient, usually about 5-11 mm. Further, the thickness of the corneal cover or corneal implant 1 is about 0.03-0.8 mm. The water content of the corneal cover or corneal implant 1 is about 20-80%, the best is from 30-70%. In accordance with some examples of the invention, the corneal cover or corneal implant 1 is made of at least one bony fish scale. Besides, the corneal cover or corneal implant 1 can be made of several bony fish scales stacked together, wherein these bony fish scales can be in the same category or not.

Referring to FIG. 2A and FIG. 2B, in accordance with some examples of the invention which relates to a contact lens 2 which is made of bony fish scales. The contact lens 2 comprises at least one bony fish scale, wherein the bony fish scales are stacked. For example, as shown in FIG. 2A and FIG. 2B, the contact lens 2 is made of bony fish scale 21 and bony fish scale 22 stacked together, wherein the bony fish scale 21 and the bony fish scale 22 can be in the same category or not.

In accordance with some examples of the invention, the bony fish scale material of the contact lens 2 is chosen from bony fish which is selected from the group consisting of the cycloid scale, and the ctenoid scale.

The contact lens 2 has a tensile strength of at least about 0.5-10 MPa. Further, the central thickness of the contact lens 2 is 0.03-0.13 mm and the diameter of the contact lens 2 is about 13-20 mm.

We would not feel comfortable when the water content of the contact lens 2 is less than 30% because the material would be too hard and the permeability of gas would be too low. On the other hand, we would not feel comfortable when the water content of the contact lens 2 is higher than 70%. That is because the water content of the contact lens 2 will always vaporize, the material itself needs to contain water content. Therefore, the contact lens 2 will suck the water from the eye. Thus, we would not feel comfortable when the water content of the contact lens 2 is higher than 70%. Besides, there is easily to have something such as protein to precipitate on the contact lens 2 when the water content of the contact lens 2 is higher than 70%. Therefore, the contact lens 2 contains 20-80% of water content, the best is from 30-70%.

Referring to FIG. 3 in accordance with some examples of the invention which relates to the flow chart of making the contact lens 2. The bony fish scales 21, 22 of the contact lens 2 may be freshly provided in a chilled or frozen manner. In a specific example of the invention, each the bony fish scales 21, 22 of the contact lens 2 having an average size less than about 20 cm in diameter may be selected for preparing the contact lens 2. Using non-ionic solution to acellularize (S11) the bony fish scales 21, 22 of the contact lens 2 avoids residual cells affecting the biocompatibility.

Because taking off the calcium content in the bony fish scales 21, 22 of the contact lens 2 can increase transparency. Therefore, by using acid solution to decalcify (S12) the bony fish scales 21, 22 of the contact lens 2, it will increase transparency of the contact lens 2.

The method for preparing the contact lens 2 of the present invention further comprises a step of cleaning (S13) the bony fish scales 21, 22 of the contact lens 2. The purpose of cleaning (S13) is getting rid of the impurities of the bony fish scales 21, 22 of the contact lens 2. The bony fish scales 21, 22 of the contact lens 2 may be cleaned by washing (S13) with other cleaning agents including but not limited to surfactant, detergent, warm water and polar solvent such as ethanol. However, the present invention is not limited to any particular cleaning step. For example, the bony fish scales 21, 22 of the contact lens 2 are cleaned enough to pass Limulus Amebocyte Lysate (LAL) test which is an assay for detection and quantitation of bacterial endotoxin. Preferably, the cleaned bony fish scales 21, 22 of the contact lens 2 would have a LAL test score less than about 20 EU/ml.

No matter what kind of the order of the three steps (S11), (S12), (S13) proceed, the step of extruding the bony fish scales 21,22 of the contact lens 2 (S14) should proceed after the three steps (S11), (S12), (S13) selection done. For example, the steps can be done in order such as (S11), (S12), (S14) or (S12), (S11), (S14) or (S11), (S12), (S13), (S14) or (S12), (S11), (S13), (S14) or (S13) (S11), (S12), (S14) or (S13) (S12), (S11), (S14) or (S11), (S13), (S12), (S14) or (S12), (S13), (S11), (S14).

After the step of decalcifying (S12) the bony fish scales 21, 22 of the contact lens 2, the contact lens 2 is extruded in a contact lens mold (S14). The step of extrusion (S14) process is to extrude one or several bony fish scale material in a contact lens mold to become the prototype. The bony fish scales 21, 22 of the contact lens 2 previously cold pressed are submitted to hot pressing performed in a desired mold at a temperature of less than 150° C. It is noted that the protein would denature when the temperature is higher than 140° C. Besides, the quality of cross linking would not be good when the temperature is lower than 80° C., preferably, about from 80° C. to 140° C. Therefore, it would be better from 80° C. to 140° C. in the step of extrusion (S14).

The heat treatment in the present invention is not limited to the extrusion (S14) described above. One skilled in the art may also adopt other heat treatments such as thermal extrusion of any type, thermal pressing and molding steps to produce the contact lens.

The method for preparing a contact lens 2 of the present invention further comprises a step of dehydrating the scale (S15). The bony fish scales 21, 22 of the contact lens 2 may be dehydrated (S15) (but not limited) after the three steps (S11), (S12), (S13) completed. In a preferred embodiment, the step of dehydrating the bony fish scales 21, 22 of the contact lens 2 (S15) proceed after the step of extruding the bony fish scales 21, 22 of the contact lens 2 (S14). The bony fish scales 21, 22 of the contact lens 2 may be dehydrated by air spraying, oven, freeze drying or any other conventional dehydration methods available so far. Also, the bony fish scales 21, 22 of the contact lens 2 may be dehydrated by soaking the bony fish scales in the ethanol or other polar organic solvent. The bony fish scales 21, 22 of the contact lens 2 are dehydrated until their water content is about 20-80%, the best is from 30-70%. In one other example, the dehydrated bony fish scales 21, 22 of the contact lens 2 (S14) may be subjected to a heat treatment at a temperature of less than about 150° C., preferably, about from 80° C. to 140° C.

After the step of extruding (S14), the contact lens 2 is cut to a suitable size (S16). The diameter of the contact lens 2 is about 13-20 mm.

After the step of cutting the contact lens 2 (S16), the contact lens 2 is sterilized (S17). The EO gas, irradiation or high pressure steam (autoclave) is used in the step of sterilizing (S17) process. These products may be further processed, for example, by extrusion (S16), and sterilizing to yield sterilized contact lenses. In a preferred embodiment, these steps may be performed with or without heating. The contact lens 2 has a tensile strength of at least about 0.5-10 MPa and the central thickness of the contact lens 2 is 0.03-0.13 mm.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A corneal cover or corneal implant to be placed within or onto the surface of the cornea is made of bony fish scales.

2. The corneal cover or corneal implant of claim 1, wherein the shape of said corneal cover or corneal implant is curvature.

3. The corneal cover or corneal implant of claim 1, wherein the diameter of said corneal cover or corneal implant is about 5-11 mm.

4. The corneal cover or corneal implant of claim 1, wherein the thickness of said corneal cover or corneal implant is 0.03-0.8 mm.

5. The corneal cover or corneal implant of claim 1, wherein the bony fish scales are selected from the group consisting of: cycloid scales and ctenoid scales.

6. The corneal cover or corneal implant of claim 1, wherein the bony fish scales comprise acellularized bony fish scales having an extruded, circular shape.

7. The corneal cover or corneal implant of claim 1, wherein the bony fish scales comprise bony fish scales in flaky form, the bony fish scales having an extruded shape.

* * * * *